United States Patent

Kanne

Patent Number: 5,565,413
Date of Patent: Oct. 15, 1996

[54] SUBSTITUTED PYRIDYL PHENYL KETONE HERBICIDES

[75] Inventor: David B. Kanne, Corte Madera, Calif.

[73] Assignee: Zeneca Limited, London, England

[21] Appl. No.: 352,009

[22] Filed: Dec. 6, 1994

[51] Int. Cl.⁶ .................................................. A01N 43/40
[52] U.S. Cl. ........................ 504/254; 546/296; 546/298
[58] Field of Search .................................. 546/296, 298; 504/254

[56] References Cited

U.S. PATENT DOCUMENTS 4,769,380  9/1988  Jones et al. ........................ 514/341

OTHER PUBLICATIONS

CA 98: 125888, Docampo et al. 1982.
CA 120: 217543 Ratemi et al. 1993.
CA 118: 233935 Singh et al. 1993.
CA 115: 29157 Singh et al. 1990.
CA 109: 54625 Kyba et al. 1988.
CA 108: 112158 Alberola et al. 1987.
CA 107: 77581 Lepikhin et al. 1986.
CA 104: 207249 Lesher et al. 1985.
CA 82: 125235 Le Guff 1974.

*Primary Examiner*—Jane Fan
*Attorney, Agent, or Firm*—Marian T. Thomson; Joseph R. Snyder

[57] ABSTRACT

Herbicidal compounds have the formula

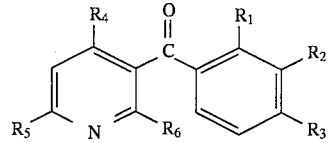

in which:

$R_1$ is hydrogen, halogen; $C_1$–$C_4$ alkyl; $C_1$–$C_4$ haloalkyl; $C_1$–$C_4$ alkoxy; $C_1$–$C_4$ haloalkoxy; $C_2$–$C_8$ alkoxyalkyl; nitro; cyano; thiocyano; or $R_7S(O)_m$- where m is 0, 1 or 2 and $R_7$ is $C_1$–$C_4$ alkyl or $C_1$–$C_4$ haloalkyl;

$R_2$ and $R_3$ are independently hydrogen; halogen; $C_1$–$C_4$ alkyl; $C_1$–$C_4$ alkoxy; $C_1$–$C_4$ haloalkyl; $C_1$–$C_4$ haloalkoxy; $C_2$–$C_8$ alkoxyalkyl; nitro; $R_8S(O)_2O$- or $R_8S(O)_n$- where n is 0, 1 or 2 and $R_8$ is $C_1$–$C_4$ alkyl, $C_1$–$C_4$ haloalkyl, $C_1$–$C_4$ cyanoalkyl, phenyl or benzyl; $NR_9R_{10}$ where $R_9$ and $R_{10}$ are independently hydrogen or $C_1$–$C_4$ alkyl; $R_{11}CO$- where $R_{11}$ is $C_1$–$C_4$ alkyl or $C_1$–$C_4$ alkoxy, $SO_2NR_{12}R_{13}$ where $R_{12}$ and $R_{13}$ are independently hydrogen, $C_1$–$C_4$ alkyl or $C_1$–$C_4$ haloalkyl, or $N(R_{14})COR_{15}$ where $R_{14}$ and $R_{15}$ are independently hydrogen or $C_1$–$C_4$ alkyl;

$R_4$ is hydrogen, halogen or hydroxy;

$R_5$ is hydrogen, methyl or trifluoromethyl; and $R_6$ is hydrogen, halogen or hydroxy;

provided that $R_4$ and $R_6$ are not both hydrogen; and agriculturally acceptable salts thereof.

17 Claims, No Drawings

SUBSTITUTED PYRIDYL PHENYL KETONE HERBICIDES

FIELD OF THE INVENTION

This invention relates to certain substituted pyridyl phenyl ketones which demonstrate herbicidal activity.

DESCRIPTION OF THE INVENTION

According to this invention, compounds of the following structure have been found to exhibit herbicidal activity:

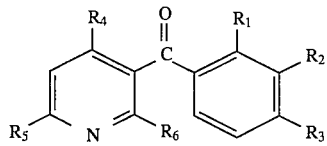

in which:

$R_1$ is hydrogen, halogen; $C_1$-$C_4$ alkyl; $C_1$-$C_4$ haloalkyl; $C_1$-$C_4$ alkoxy; $C_1$-$C_4$ haloalkoxy; $C_2$-$C_8$ alkoxyalkyl; nitro; cyano; thiocyano; or $R_7S(O)_m$- where m is 0, 1 or 2 and $R_7$ is $C_1$-$C_4$ alkyl or $C_1$-$C_4$ haloalkyl;

$R_2$ and $R_3$ are independently hydrogen; halogen; $C_1$-$C_4$ alkyl; $C_1$-$C_4$ alkoxy; $C_1$-$C_4$ haloalkyl; $C_1$-$C_4$ haloalkoxy; $C_2$-$C_8$ alkoxyalkyl; nitro; $R_8S(O)_2O$- or $R_8S(O)_n$- where n is 0, 1 or 2 and $R_8$ is $C_1$-$C_4$ alkyl, $C_1$-$C_4$ haloalkyl, $C_1$-$C_4$ cyanoalkyl, phenyl or benzyl; $NR_9R_{10}$ where $R_9$ and $R_{10}$ are independently hydrogen or $C_1$-$C_4$ alkyl; $R_{11}CO$- where $R_{11}$ is $C_1$-$C_4$ alkyl or $C_1$-$C_4$ alkoxy, $SO_2NR_{12}R_{13}$ where $R_{12}$ and $R_{13}$ are independently hydrogen, $C_1$-$C_4$ alkyl or $C_1$-$C_4$ haloalkyl, or $N(R_{14})COR_{15}$ where $R_{14}$ and $R_{15}$ are independently hydrogen or $C_1$-$C_4$ alkyl;

$R_4$ is hydrogen, halogen or hydroxy;

$R_5$ is hydrogen, methyl or trifluoromethyl; and $R_6$ is hydrogen, halogen or hydroxy;

where $R_4$ and $R_6$ may be the same or different provided that $R_4$ and $R_6$ are not both hydrogen and when $R_4$ and $R_6$ are both halogen, the halogens may be identical or different;

and agriculturally acceptable salts thereof.

Preferably:

$R_1$ is other than hydrogen, most preferably halogen, methyl, trifluoromethyl, methoxy, trifluoromethoxy, or nitro;

$R_2$ and $R_3$ are independently hydrogen, halogen, $C_1$-$C_4$ alkyl, $C_1$-$C_4$ alkoxy, trifluoromethyl, trifluoromethoxy, nitro, $R_8S(O)_2O$- or $R_8S(O)_n$- where n is 0, 1 or 2 and $R_8$ is methyl, ethyl or chloromethyl; $C_2$-$C_6$ alkoxyalkyl, or $SO_2NR_{12}R_{13}$; provided that $R_2$ and $R_3$ are not both hydrogen; and $R_4$ is hydroxy.

In one preferred embodiment, $R_4$ and $R_6$ are both hydroxy. In another preferred embodiment, $R_4$ is hydroxy and $R_6$ is halogen.

Because of tautomerism, either or both of the hydroxy groups represented by $R_4$ or $R_6$ may exist in the keto form, i.e.:

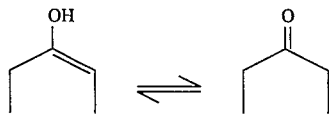

and similarly the bridging carbonyl group may take either form:

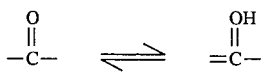

so that it would be apparent to those skilled in the art that the compounds of this invention may have a number of different structural formulae.

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants", is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, as pre- and/or post-emergent herbicides. Pre-emergence herbicides are applied prior to emergence of vegetation from the soil; post-emergence herbicides are applied to control or kill existing vegetation.

Compounds of this invention in which $R_4$ and $R_6$ are both halogen may be produced from the corresponding dihalopyridines by metallation with lithium diisopropyl amide, lithium tetramethylpiperidide or other strong base, quenching with the appropriate benzaldehyde to form a carbinol, then oxidizing this carbinol to the ketone, for instance with manganese dioxide or chromium trioxide or via the Swern oxidation with oxalyl chloride.

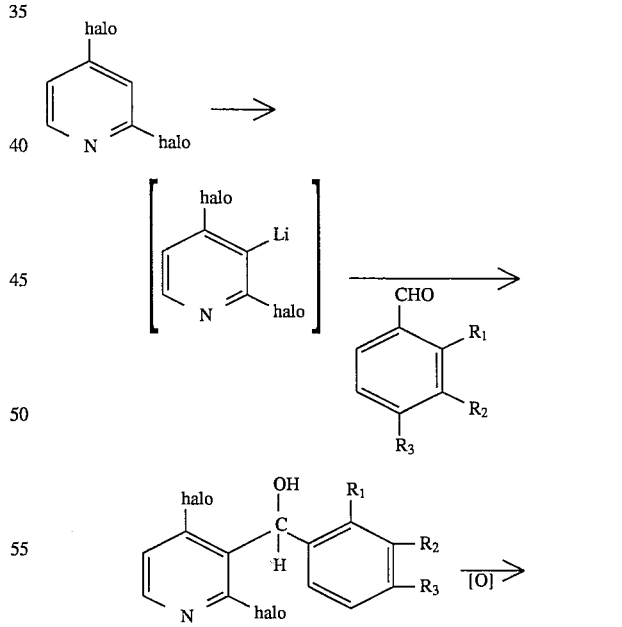

Compounds in which $R_4$ is hydroxy may be produced from the dihalo compounds by treatment with one equivalent of benzyl oxide to produce the benzyl ether, which may then be removed hydrogenolytically with palladium or with saturated HBr:

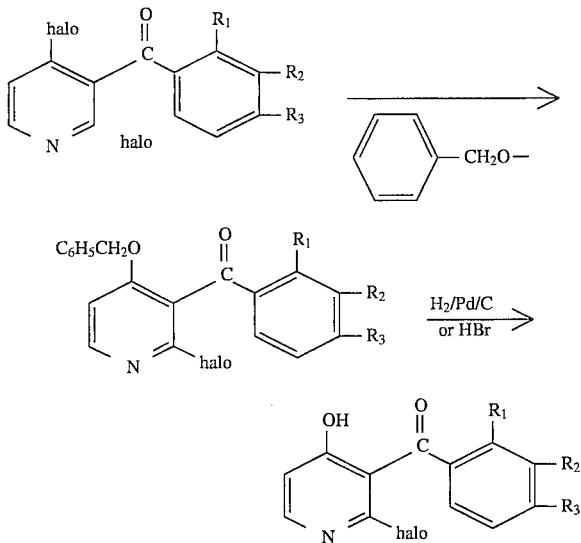

Compounds in which both $R_4$ and $R_6$ are hydroxy are similarly produced using two equivalents of benzyl oxide, or in some cases may be made by reaction of 2,4-dihydroxypyridine and the appropriate benzoic acid in polyphosphoric acid and at elevated temperatures.

The following are representative examples of preparation of compounds of this invention.

EXAMPLE 1

Preparation of 2,4-difluoro-3-(3-ethoxy-2-methyl-4-methylsulfonylbenzoyl)-pyridine (Compound No. 4)

(a) To a solution of 0.97 g (9.6 mmol) diisopropylamine in 9 ml tetrahydrofuran (THF) was added 3.7 ml (9.1 mmol) n-butyllithium in hexane dropwise. The solution was stirred at −70° C. for 20 minutes, warmed briefly to −40° C., then again chilled to −70° C. A solution of 1.00 g (8.70 mmol) 2,4-difluoropyridine in 5 ml THF was added dropwise. The resulting light brown mixture was stirred for 50 minutes at −70° C., then a solution of 2-methyl-3-ethoxy-4-(methylsulfonyl)-benzaldehyde in 9 ml THF was added dropwise. The benzaldehyde may be prepared by reduction of the corresponding benzoic aid, which may be prepared by the process described in U.S. Pat. No. 5,110,979. The resulting brown mixture was stirred at −70° C. under nitrogen for 1¾ hours, then quenched with 10 ml saturated ammonium chloride solution, followed by 50 ml ether. The organic phase was washed, filtered and evaporated, yielding 2.65 g of a viscous orange oil, identified spectroscopically as the carbinol corresponding to the desired product.

(b) To a solution of the product of step (a) (2.6 g, 7.3 mmol) in toluene (30 ml) was added manganese dioxide (3.17 g, 36 mmol). The mixture was stirred with vigorous refluxing for 5 hours, then filtered. The filter cake was washed with toluene, and the toluene stripped to produce an orange oil. The crude product was purified chromatographically, producing an orange semi-solid material, identified spectroscopically as the desired product.

EXAMPLE 2

Preparation of 3-3-ethoxy-2-methyl-4-methylsulfonylbenzoyl)-2-fluoro-4-hydroxypyridine (Compound No. 13)

(a) To a solution containing 245 mg (0.758 mmol) of the product of Example 1 in 3 ml THF maintained at −20° C. under nitrogen was added dropwise a solution of benzyloxide generated in 0.5 ml THF from 61.4 mg (0.564 mmol) benzyl alcohol and 24 mg (0.597 mmol) sodium hydride (oil-free). The mixture was allowed to warm slowly to room temperature, with stirring. It was then combined with 20 ml ether, washed, dried and filtered. Stripping of solvent produced 255 mg of an orange oil, which was then purified chromatographically, yielding 102 mg of a yellow oil which soon solidified. Spectroscopic analysis showed the desired benzylated material.

(b) Product of step (a) (71 mg, 0.16 mmol) was mixed with 14 mg of 10% palladium/carbon catalyst and 1 g dioxane. The mixture was shaken for 9½ hours; additional 7 mg of catalyst was added and this mixture shaken for 2 more hours, when the reaction was complete. The mixture was filtered and solvent stripped off, yielding 53.7 mg of a light brown solid, identified spectroscopically as the desired product.

EXAMPLE 3

Preparation of 3-(3-ethoxy-2-methyl-4-methylsulfonylbenzoyl)-2,4-pyridinedione (Compound No. 6)

(a) To a solution of 2.21 g diisopropylamine in 20 ml tetrahydrofuran THF at −65° C. under nitrogen was added 8.3 ml of 2.5M n-butyl lithium in hexane dropwise. The solution was stirred at −65° C. for 30 minutes, then a solution of 3.13 g (19.8 mmol) dichloropyridine in 5 ml of THF was added. The resulting brown solution was stirred at −70° C. for 45 minutes, then a solution of 2.4 g (9.92 mmol) 3-ethoxy-2-methyl-4-methylsulfonylbenzaldehyde in 10 ml of THF was added. The mixture was stirred vigorously at −70° C. under nitrogen for 1 hour, then quenched with 20 ml water saturated with ammonium chloride. This solution was partitioned with 50 ml of ether. The ether layer was washed, dried and evaporated in vacuo to yield 5.4 g of a brown oil. This material was heated to 70° C. (0.01 mm Hg) to remove residual dichloropyridine, leaving 3.57 g of 2,4-dichloro-3-(1-hydroxy-3'-ethoxy-2'-methyl-4'-methylsulfonylbenzyl)pyridine.

(b) To the product of step (a) in 30 ml of toluene was added 4 g manganese dioxide. The suspension was refluxed for 7 hours with mechanical stirring and with azeotropic removal of water. The mixture was filtered and the filter cake washed with ether. The solvent was evaporated in vacuo to yield 2.08 g of 2,4-dichloro-3-(3-ethoxy-2-methyl-4-methylsulfonylbenzoyl)pyridine as a brown semi-solid.

(c) To a solution of the product of step (b) (0.49 g, 1.26 mmol) in 5 ml THF at −20° C. under nitrogen was added a slurry of benzyl oxide (73.78 mmol) generated from benzyl alcohol and oil free sodium hydride in 2 ml THF. The reaction mixture was allowed to warm to room temperature and stirred for several hours, then partitioned between ether and water. The organic layers were dried and evaporated to yield 0.5 g of a crude product. This was purified via chromatography on silica gel using 25% ethyl acetate in hexanes as the eluant to give 0.177 g of 2,4-dibenzyloxy- 3-(3-ethoxy-2-methyl-4-methylsulfonylbenzoyl)pyridine, a viscous yellow oil.

(d) To a solution of the product of step (c) (0.387 g) in 8 ml dioxane was added 110 mg of 10% palladium on carbon (Degussa type, water wet). The mixture was then shaken for 5 hours, filtered and the filter cake washed. The solvents were evaporated to yield 260 mg of 4-hydroxy-3-(3-ethoxy-2-methyl-4-methylsulfonylbenzoyl)pyrid-2-one.

EXAMPLE 4

Preparation of
3-(2,4-dichlorobenzoyl)pyridine-2,4-dione
(Compound No. 1)

This example illustrates production of a compound of this invention by reaction of 2,4-dihydroxypyridine with a substituted benzoic acid.

In a flask were combined 5 g (0.045 mmol) 2,4-dihydroxypyridine 8.6 g (0.045 mmol) 2,4-dichlorobenzoic acid and 50 g polyphosphoric acid. The mixture was heated to 180° C. for 3 hours. while the reaction mixture was still warm it was poured into a beaker, then worked up with ice and methylene chloride, yielding 0.58 g of crude product.

Spectroscopic analyses of the crude product showed the presence of the desired product in low yield, together with material identified as

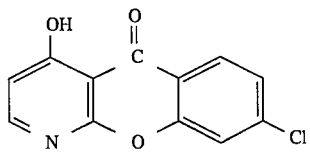

or an isomer thereof.

Table I depicts representative compounds of this invention, prepared by a process as described above. Most compounds were obtained as oils. Structures were confirmed by spectroscopic analyses.

TABLE I

| Cmpd. No. | $R_1$ | $R_2$ | $R_3$ | $R_4$ | $R_5$ | $R_6$ |
|---|---|---|---|---|---|---|
| 1 | Cl | H | Cl | OH | H | OH |
| 2 | H | H | H | Cl | H | Cl |
| 3 | $CH_3$ | $OC_2H_5$ | $SO_2CH_3$ | Cl | H | Cl |
| 4 | $CH_3$ | $OC_2H_5$ | $SO_2CH_3$ | F | H | F |
| 5 | Cl | H | Cl | F | H | F |
| 6 | $CH_3$ | $OC_2H_5$ | $SO_2CH_3$ | OH | H | OH |
| 7 | Cl | H | Cl | H | $CF_3$ | OH |
| 8 | Cl | H | Cl | OH | H | Cl |
| 9 | Cl | H | Cl | OH | $CH_3$ | OH |
| 10 | $CH_3$ | $OC_2H_5$ | $SO_2CH_3$ | OH | H | H |
| 11 | $CH_3$ | $OC_2H_5$ | $SO_2CH_3$ | OH | H | Cl |
| 12 | $CH_3$ | H | $SO_2CH_3$ | OH | H | OH |
| 13 | $CH_3$ | $OC_2H_5$ | $SO_2CH_3$ | OH | H | F |
| 14 | $CH_3$ | H | $SCH_3$ | OH | H | OH |
| 15 | $CH_3$ | H | $S(O)CH_3$ | OH | H | OH |

Herbicidal Activity Tests

Compounds of Table I were tested for herbicidal activity as follows:

PRE-EMERGENCE HERBICIDAL EVALUATION

On the day preceding treatment, seeds of several different weed species were planted in a sandy loam soil containing only trace organic matter. Propagules were sown in individual rows using one species per row across the width of a flat. The grass weeds planted were green foxtail (*Setaria viridis*) (SETVI), wild oat (*Arena fatua*) (AVEFA) and barnyard-grass (*Echinochloa crus-galli*) (ECHCG). Broadleaf weeds utilized were wild mustard (*Sinapis arvensis*) (SINAR), velvetleaf (*Abutilon theophrasti*) (ABUTH), and annual morningglory (Ipomoea spp.) (IPOSS) or tall morningglory (*Ipomoea purpurea*) (PHBPU). Additionally, yellow nutsedge (*Cyperus esculentus*) (CYPES) nutlets were sown. Seeding depths ranged from 1.0 to 1.5 cm and plant densities ranged from 3 to 25 plants per row depending on individual plant species.

Solutions of the test compounds were prepared by weighing out 74.7 mg of the test compound into a bottle, then dissolving the compound in 7 ml of acetone containing 1% v/v Tween 20' (polyoxyethylene sorbitan monolaurate emulsifier) as a surfactant and then adding 7 ml of deionized water to reach a 14 ml final volume. Tween 20' content was 0.5% v/v of the final spray volume. Additional solvents, not exceeding 2 ml (15% of spray volume), were used if needed to dissolve the compound.

The soil surface was sprayed inside an enclosed linear spray table with the nozzle set at 30.5 cm (12 inches) above the soil line. The spray table was calibrated to deliver 748 L/ha (80 gal/A) with the application rate being between 0.5 kg/ha and 4 kg/ha as indicated. After treatment the flats were placed into a greenhouse and watered overhead by sprinkling. The greenhouse environmental systems provided the plants with natural and artificial (via metal halide lamps) lighting to attain 14 hours of light per day. Day and night temperatures were maintained at 29° and 21° C. respectively.

The degree of weed control was evaluated and recorded 17–21 days after treatment as a percentage of weed control as compared to the growth of the same species of the same age in an untreated control flat. Percent control is the total injury to the plants due to all factors including inhibited emergence, stunting, malformation, chlorosis and other types of plant injury. The control ratings range from 0 to 100 percent, where 0% represents no effect with growth equal to the untreated control and where 100% represents complete kill. The results of such pre-emergence testing are summarized in Table II below. A dash indicates that no test was performed at that level of application.

POST-EMERGENCE HERBICIDAL
EVALUATION

The soil was prepared and seeded with the same species and methodology described for the pre-emergence test. Post-emergence flats were placed in the greenhouse under the same environmental conditions as described for the pre-emergence flats and watered overhead by sprinkling. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was between 0.5 kg/has and 4 kg/ha, and as indicated. Treated plants were then returned to a greenhouse and watered daily without wetting the foliage. The degree of weed control was evaluated 17 to 21 days after application and recorded as percentage of control as compared to the growth of the same species in an untreated control flat of the same age. The percent control scale (0–100%) used to evaluate the pre-emergence treatment was also applied to the post-emergence treatment. A dash indicates that no test was performed at the level of application. The results of such post-emergence testing are summarized in Table III below.

matic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

TABLE II

Pre-Emergence Testing

| Compound No. | Rate (kg/ha) | AVEFA | ECHCG | SETVI | ABUTH | PHBPU | IPOSS | SINAR | CYPES |
|---|---|---|---|---|---|---|---|---|---|
| 1 | 1.5 | 70 | 95 | 98 | 100 | 60 | — | 100 | 85 |
| 2 | 4.0 | 0 | 75 | 60 | 10 | 0 | — | 100 | 5 |
| 3 | 1.2 | 20 | 20 | 90 | 0 | 10 | — | 0 | 0 |
| 4 | 4.0 | 60 | 100 | 90 | 100 | 70 | — | 100 | 85 |
| 5 | 4.0 | 0 | 0 | 10 | 75 | — | 10 | 40 | 5 |
| 6 | 0.5 | 95 | 100 | 100 | 100 | — | 85 | 100 | 90 |
| 7 | 4.0 | 30 | 70 | 90 | 50 | — | 5 | 5 | 0 |
| 8 | 4.0 | 0 | 0 | 0 | 0 | — | 0 | 0 | 0 |
| 9 | 1.5 | 60 | 95 | 100 | 100 | — | 40 | 85 | 60 |
| 10 | 0.75 | 0 | 0 | 0 | 100 | — | 40 | 25 | 5 |
| 11 | 1.6 | 0 | 0 | 0 | 80 | — | 5 | 0 | 0 |
| 12 | 0.82 | 70 | 100 | 85 | 100 | — | 90 | 95 | 90 |
| 13 | 1.0 | 90 | 100 | 100 | 100 | — | 95 | 100 | 95 |
| 14 | 1.0 | 10 | 100 | 100 | 100 | — | 95 | 50 | 80 |
| 15 | 1.0 | 95 | 100 | 80 | 100 | — | 60 | 25 | 98 |

TABLE III

Post-Emergence Testing

| Compound No. | Rate (kg/ha) | AVEFA | ECHCG | SETVI | ABUTH | PHBPU | IPOSS | SINAR | CYPES |
|---|---|---|---|---|---|---|---|---|---|
| 1 | 1.5 | 95 | 90 | 90 | 85 | 95 | — | 100 | 60 |
| 2 | 4.0 | 0 | 0 | 0 | 10 | 5 | — | 30 | 0 |
| 3 | 1.2 | 0 | 0 | 10 | 30 | 25 | — | 0 | 0 |
| 4 | 4.0 | 60 | 95 | 80 | 100 | 85 | — | 100 | 85 |
| 5 | 4.0 | 0 | 5 | 10 | 75 | — | 50 | 100 | 10 |
| 6 | 0.5 | 100 | 100 | 100 | 100 | — | 98 | 100 | 100 |
| 7 | 4.0 | 10 | 30 | 40 | 90 | — | 90 | 100 | 5 |
| 8 | 4.0 | 5 | 100 | 15 | 0 | — | 15 | 100 | 5 |
| 9 | 1.5 | 40 | 90 | 80 | 100 | — | 50 | 100 | 70 |
| 10 | 0.75 | 0 | 0 | 0 | 90 | — | 75 | 60 | 5 |
| 11 | 1.6 | 0 | 75 | 5 | 70 | — | 5 | 15 | 20 |
| 12 | 0.82 | 98 | 98 | 90 | 100 | — | 98 | 100 | 90 |
| 13 | 1.0 | 40 | 100 | 60 | 100 | — | 100 | 100 | 90 |
| 14 | 1.0 | 90 | 100 | 70 | 100 | — | 95 | 90 | 85 |
| 15 | 1.0 | 80 | 100 | 95 | 100 | — | 90 | 100 | 80 |

The results above illustrate the pre-emergent and post-emergent efficacy of the present compounds against a variety of weed species.

In practice, a pure compound can be used as an herbicide. However, in general, the compounds are first formulated with one or more inert carriers or diluents suitable for herbicidal user before being applied.

The compositions or formulations, including a compound as described herein, may exist in any one of a number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aro- To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrenebutadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

EXAMPLES OF TYPICAL COMPOSITIONS

| Ingredient | Weight % | | |
|---|---|---|---|
| Oil | | | |
| Active Compound | 1 | | |
| Oil solvent-heavy aromatic naphtha | 99 | | |
| Total | 100 | | |
| Emulsifiable Concentrate | | | |
| Active Compound | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Active Compound | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention may be other pesticidal agents, such as herbicides, fungicides, insecticides, acaricides, nematocides, bactericides, and plant growth regulators. Such compositions may also contain soil disinfectants or fumigalnts and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application.

Examples of useful complementary herbicides include:

A. Benzo-2,1,3-thiodiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;
[*These compounds are preferably employed in combination with a safener such as 2,2-dichloro-N-di-2-propenylacetamide (dichloromid).]

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, flurogylcofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim and salts thereof, sulcotrione, sethoxydim, cycloxydim, tralkoxydim, and clethodim;

U. sulfony urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

Although the invention has been described with reference to preferred embodiments and examples thereof, it is not intended that the present invention be limited to only those described embodiments. The description of the preferred embodiments contained herein is intended in no way to limit the scope of the invention. As will be appreciated by a person skilled in the art, modifications and adaptations of the above-described invention can be made without departing from the spirit and scope of the invention, which is defined and circumscribed by the appended claims.

What is claimed is:

1. A compound having the formula

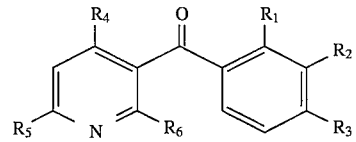

in which:

$R_1$ is hydrogen, halogen; $C_1$–$C_4$ alkyl; $C_1$–$C_4$ haloalkyl; $C_1$–$C_4$ alkoxy; $C_1$–$C_4$ haloalkoxy; $C_2$–$C_8$ alkoxyalkyl; nitro; cyano; thiocyano; or $R_7S(O)_m$- where m is 0, 1 or 2 and $R_7$ is $C_1$–$C_4$ alkyl or $C_1$–$C_4$ haloalkyl;

$R_2$ and $R_3$ are independently hydrogen; halogen; $C_1$–$C_4$ alkyl; $C_1$–$C_4$ alkoxy; $C_1$–$C_4$ haloalkyl; $C_1$–$C_4$ haloalkoxy; $C_2$–$C_8$ alkoxyalkyl; nitro; $R_8S(O)_2O$- or $R_8 S(O)_n$- where n is 0, 1 or 2 and $R_8$ is $C_1$–$C_4$ alkyl, $C_1$–$C_4$ haloalkyl, $C_1$–$C_4$ cyanoalkyl, phenyl or benzyl; $NR_9R_{10}$ where $R_9$ and $R_{10}$ are independently hydrogen or $C_1$–$C_4$ alkyl; $R_{11}CO$- where $R_{11}$ is $C_1$–$C_4$ alkyl or $C_1$–$C_4$ alkoxy; $SO_2NR_{12}R_{13}$ where $R_{12}$ and $R_{13}$ are independently hydrogen, $C_1$–$C_4$ alkyl or $C_1$–$C_4$ haloalkyl; or $N(R_{14})COR_{15}$ where $R_{14}$ and $R_{15}$ are independently hydrogen or $C_1$–$C_4$ alkyl;

$R_4$ is halogen or hydroxy;

$R_5$ is hydrogen, methyl or trifluoromethyl; and $R_6$ is hydrogen, halogen or hydroxy; with the proviso that when $R_4$ is halogen $R_6$ is not hydroxy:

or an agriculturally acceptable salt thereof.

2. A compound according to claim 1 in which $R_1$ is other than hydrogen.

3. A compound according to claim 1 in which $R_4$ is hydroxy and $R_6$ is halogen.

4. A compound according to claim 3 in which $R_1$ is methyl, halogen, trifluoromethyl, methoxy, trifluoromethoxy or nitro; and $R_2$ and $R_3$ are independently hydrogen, halogen, $C_1$–$C_2$ alkyl, $C_1$–$C_2$ alkoxy, trifluoromethyl, trifluoromethoxy, nitro, $R_8S(O)_2O$- or $R_8S(O)_n$ where $R_8$ is methyl, ethyl or chloromethyl and n is 0, 1 or 2, $C_2$–$C_6$ alkoxyalkyl, or $SO_2NR_{12}R_{13}$; provided that $R_2$ and $R_3$ are not both hydrogen.

5. A compound according to claim 1 in which both $R_4$ and $R_6$ are hydroxy.

6. A compound according to claim 5 in which $R_1$ is methyl, halogen, trifluoromethyl, methoxy, trifluoromethoxy or nitro; and $R_2$ and $R_3$ are independently hydrogen, halogen, $C_1$–$C_2$ alkyl, $C_1$–$C_2$ alkoxy, trifluoromethyl, trifluoromethoxy, nitro, $R_8S(O)_2O$- or $R_8S(O)_n$ where $R_8$ is methyl, ethyl or chloromethyl and n is 0, 1 or 2, $C_2$–$C_6$ alkoxyalkyl, or $SO_2NR_{12}R_{13}$; provided that $R_2$ and $R_3$ are not both hydrogen.

7. A compound according to claim 1 in which $R_4$ and $R_6$ are both halogen.

8. A compound according to claim 1 in which $R_1$ and $R_3$ are both chloro, $R_2$ and $R_5$ are both hydrogen, and $R_4$ and $R_6$ are both hydroxy.

9. A compound according to claim 1 in which $R_1$ is methyl, $R_2$ is ethoxy, $R_3$ is methylsulfonyl, and $R_5$ is hydrogen.

10. A compound according to claim 9 in which $R_4$ and $R_6$ are both fluoro.

11. A compound according to claim 9 in which $R_4$ and $R_6$ are both hydroxy.

12. A compound according to claim 9 in which $R_4$ is hydroxy and $R_6$ is fluoro.

13. A compound according to claim 1 in which $R_1$ is methyl, $R_2$ and $R_5$ are both hydrogen, $R_3$ is methylsulfonyl and $R_4$ and $R_6$ are both hydroxy.

14. A compound according to claim 1 in which $R_1$ is methyl, $R_2$ and $R_5$ are both hydrogen, $R_3$ is methylthio, and $R_4$ and $R_6$ are both hydroxy.

15. A compound according to claim 1 in which $R_1$ is methyl, $R_2$ and $R_5$ are both hydrogen, $R_3$ is methylsulfinyl and $R_4$ and $R_6$ are both hydroxy.

16. An herbicidal composition comprising:

(a) an herbicidally effective amount of a compound having the formula

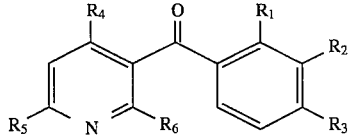

in which:

$R_1$ is hydrogen, halogen; $C_1$–$C_4$ alkyl; $C_1$–$C_4$ haloalkyl; $C_1$–$C_4$ alkoxy; $C_1$–$C_4$ haloalkoxy; $C_2$–$C_8$ alkoxyalkyl; nitro; cyano; thiocyano; or $R_7S(O)_m$- where m is 0, 1 or 2 and $R_7$ is $C_1$–$C_4$ alkyl or $C_1$–$C_4$ haloalkyl;

$R_2$ and $R_3$ are independently hydrogen; halogen; $C_1$–$C_4$ alkyl; $C_1$–$C_4$ alkoxy; $C_1$–$C_4$ haloalkyl; $C_1$–$C_4$ haloalkoxy; $C_2$–$C_8$ alkoxyalkyl; nitro; $R_8S(O)_2O$- or $R_8S(O)_n$- where n is 0, 1 or 2 and $R_8$ is $C_1$–$C_4$ alkyl, $C_1$–$C_4$ haloalkyl, $C_1$–$C_4$ cyanoalkyl, phenyl or benzyl; $NR_9R_{10}$ where $R_9$ and $R_{10}$ are independently hydrogen or $C_1$–$C_4$ alkyl; $R_{11}CO$- where $R_{11}$ is $C_1$–$C_4$ alkyl or $C_1$–$C_4$ alkoxy; $SO_2NR_{12}R_{13}$ where $R_{12}$ and $R_{13}$ are independently hydrogen, $C_1$–$C_4$ alkyl or $C_1$–$C_4$ haloalkyl; or $N(R_{14})COR_{15}$ where $R_{14}$ and $R_{15}$ are independently hydrogen or $C_1$–$C_4$ alkyl;

$R_4$ is halogen or hydroxy;

$R_5$ is hydrogen, methyl or trifluoromethyl; and $R_6$ is hydrogen, halogen or hydroxy;

with the proviso that when $R_4$ is halogen $R_6$ is not hydroxy;

or an agriculturally acceptable salt thereof; and (b) an agriculturally acceptable diluent or carrier therefor.

17. A method of controlling undesirable vegetation comprising applying to said vegetation or the locus thereof an herbicidally effective amount of a compound having the formula

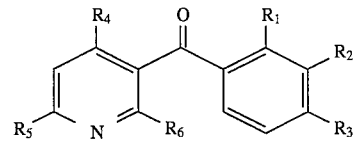

in which:

$R_1$ is hydrogen, halogen; $C_1$–$C_4$ alkyl; $C_1$–$C_4$ haloalkyl; $C_1$–$C_4$ alkoxy; $C_1$–$C_4$ haloalkoxy; $C_2$–$C_8$ alkoxyalkyl; nitro; cyano; thiocyano; or $R_7S(O)_m$- where m is 0, 1 or 2 and $R_7$ is $C_1$–$C_4$ alkyl or $C_1$–$C_4$ haloalkyl;

$R_2$ and $R_3$ are independently hydrogen; halogen; $C_1$–$C_4$ alkyl; $C_1$–$C_4$ alkoxy; $C_1$–$C_4$ haloalkyl; $C_1$–$C_4$ haloalkoxy; $C_2$–$C_8$ alkoxyalkyl; nitro; $R_8S(O)_2$ O- or $R_8S(O)_n$- where n is 0, 1 or 2 and $R_8$ is $C_1$–$C_4$ alkyl, $C_1$–$C_4$ haloalkyl, $C_1$–$C_4$ cyanoalkyl, phenyl or benzyl; $NR_9R_{10}$ where $R_9$ and $R_{10}$ are independently hydrogen or $C_1$–$C_4$ alkyl; $R_{11}CO$- where $R_{11}$ is $C_1$–$C_4$ alkyl or $C_1$–$C_4$ alkoxy; $SO_2 NR_{12}R_{13}$ where $R_{12}$ and $R_{13}$ are independently hydrogen, $C_1$–$C_4$ alkyl or $C_1$–$C_4$ haloalkyl; or $N(R_{14})COR_{15}$ where $R_{14}$ and $R_{15}$ are independently hydrogen or $C_1$–$C_4$ alkyl;

$R_4$ is hydrogen, halogen or hydroxy;

$R_5$ is hydrogen, methyl or trifluoromethyl; and $R_6$ is hydrogen, halogen or hydroxy;

wherein $R_4$ and $R_6$ may be identical or different provided that $R_4$ and $R_6$ are not both hydrogen;

or an agriculturally acceptable salt thereof.

* * * * *

UNITED STATES PATENT AND TRADEMARK OFFICE
CERTIFICATE OF CORRECTION

PATENT NO. : 5,565,413
DATED : October 15, 1996
INVENTOR(S) : David B. Kanne

It is certified that error appears in the above-indentified patent and that said Letters Patent is hereby corrected as shown below:

Col. 12, line 37, delete "halogen or"

Col. 12, lines 39-40, delete "with the proviso that when $R_4$ is halogen $R_6$ is not hydroxy:"

Col. 12, lines 64-65, delete "7. A compound according to claim 1 in which $R_4$ and $R_6$ are both halogen."

Col. 13, lines 4-5, delete "10. A compound according to claim 9 in which $R_4$ and $R_6$ are both fluoro."

Col. 13, line 45, delete "halogen or"

Col. 14, lines 4-5, delete "with the proviso that when $R_4$ is halogen $R_6$ is not hydroxy;"

Signed and Sealed this

Second Day of September, 1997

Attest:

BRUCE LEHMAN

*Attesting Officer*  *Commissioner of Patents and Trademarks*